(12) United States Patent
Weibel et al.

(10) Patent No.: US 9,714,367 B1
(45) Date of Patent: Jul. 25, 2017

(54) LIGHT CURABLE ADHESIVES

(71) Applicant: Verily Life Sciences LLC, Mountainview, CA (US)

(72) Inventors: Douglas Weibel, Madison, WI (US); Babak Parviz, Los Altos, CA (US); Eden Rephaeli, Menlo Park, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 14/584,012

(22) Filed: Dec. 29, 2014

Related U.S. Application Data

(60) Provisional application No. 62/059,794, filed on Oct. 3, 2014.

(51) Int. Cl.

| | |
|---|---|
| *A61L 24/04* | (2006.01) |
| *C08F 2/50* | (2006.01) |
| *A61B 17/03* | (2006.01) |
| *C09J 11/04* | (2006.01) |
| *C09J 4/00* | (2006.01) |
| *A61K 31/785* | (2006.01) |
| *C08K 3/08* | (2006.01) |
| *B01J 19/12* | (2006.01) |

(52) U.S. Cl.
CPC ............ *C09J 11/04* (2013.01); *A61K 31/785* (2013.01); *B01J 19/127* (2013.01); *C08K 3/08* (2013.01); *C09J 4/00* (2013.01); *B01J 2219/1203* (2013.01); *C08K 2003/0806* (2013.01); *C08K 2003/0831* (2013.01)

(58) Field of Classification Search
None
See application file for complete search history.

(56) References Cited

U.S. PATENT DOCUMENTS

| | | | | |
|---|---|---|---|---|
| 2006/0035087 | A1* | 2/2006 | Yadav | C03C 27/10 428/411.1 |
| 2012/0089180 | A1* | 4/2012 | Fathi | B41J 2/17559 606/214 |
| 2012/0231197 | A1* | 9/2012 | Mitchell | B32B 7/06 428/40.2 |
| 2012/0283336 | A1* | 11/2012 | Grigorenko | B22F 1/0022 514/769 |
| 2014/0220082 | A1* | 8/2014 | Stewart | C09J 133/26 424/400 |
| 2015/0315434 | A1* | 11/2015 | Steele | C09J 101/08 514/772.1 |

OTHER PUBLICATIONS

Link, S. and El-Sayed, M. A. "Size and Temperature Dependence of the Plasmon Absorption of Colloidal Gold Nanoparticles" J. Phys. Chem. B 1999, 103, 4212-4217 (May 7, 1999).

"Gold Nanoparticles: Properties and Appications" Sigma-Aldrich, http://www.sigmaaldrich.com/materials-science/nanomaterials/gold-nanoparticles.html, p. 1-5 (Jan. 7, 2012).

"Gold Nanoparticles: Optical Properties" NanoComposix, http://nanocomposix.com/pages/gold-nanoparticies-optical-properties, p. 1-6 (Aug. 8, 2014).

\* cited by examiner

*Primary Examiner* — Haejin Sarah Park
(74) *Attorney, Agent, or Firm* — McDonnell Boehnen Hulbert & Berghoff LLP

(57) ABSTRACT

A system that includes a polymer adhesive containing metallic or other nanoparticles that resonate upon the application of electromagnetic radiation to product heat. Heat generated by particle resonance is used to cure the polymer adhesive. Applications include wound repair, and industrial, commercial and craft applications.

15 Claims, 2 Drawing Sheets

Gold

LIGHT CURABLE ADHESIVES

RELATED APPLICATION

This application claims the benefit of U.S. provisional patent application Ser. No. 62/059,794, filed Oct. 3, 2014, the disclosure of which is incorporated by reference herein in its entirety.

BACKGROUND

Field

The disclosure is directed to adhesives containing nanoparticles that are curable through the application of electromagnetic radiation.

Related Art

Polymer adhesives are used in a variety of applications ranging from industrial processes to recreational crafts. The ability of these adhesives to function as bonding agents involves a two-step process generally referred to as setting and curing. Setting refers to the transition of a resin in liquid form (pre-polymer) to an immature polymer with limited mechanical properties. Curing refers to the transition of the immature polymer to its final state in which the mechanical and physical properties no longer change. The time required for setting and curing vary widely, depending on the polymer. For some adhesives, the application of heat hastens the cure time.

One application for polymer adhesives is surgery. Tissue adhesives (TAs) are a class of organic polymers used very widely in surgery to close an incision and provide mechanical support during wound healing. The physical barrier created by TAs reduces microbial access to the wound and decreases the frequency of infections. In a typical process, wound edges are approximated and TA prepolymers (which are liquid at room temperature) are applied to the skin surface. Upon setting and curing, the polymer bonds to the tissue edges and holds the approximated incision closed. A major challenge in the application of TAs is the time scale for the polymer to achieve full mechanical properties. This characteristic limits the application and stand-alone use of tissue adhesives.

SUMMARY

In one aspect, the disclosure is directed to a system that includes a polymer resin including a nanoparticle that has an electromagnetic radiation absorbance maximum and electromagnetic radiation source that emits light at a wavelength that matches the absorbance maximum of the nanoparticle.

In another aspect, the disclosure is directed to a method for at least partially curing a polymer adhesive containing metallic nanoparticles. The method includes applying electromagnetic radiation to the adhesive at a wavelength or a range of wavelengths that include an absorption maxima of the particles.

In yet another aspect, the disclosure is directed to a method for closing a wound. The method includes applying to the wound a polymer adhesive including metallic nanoparticles and at least partially curing the adhesive by directing electromagnetic radiation to the adhesive, wherein the electromagnetic radiation includes a wavelength of an absorbance maxima of the nanoparticles.

In these and other aspects of the disclosure, the nanoparticles may be noble metal nanoparticles. In addition, the nanoparticles may have a diameter of about 5 to about 500 nanometers. The polymer may be one of an acrylate, epoxy, silicone, urethane, methacrylate, and polysulfide.

DESCRIPTION

Figure 1:
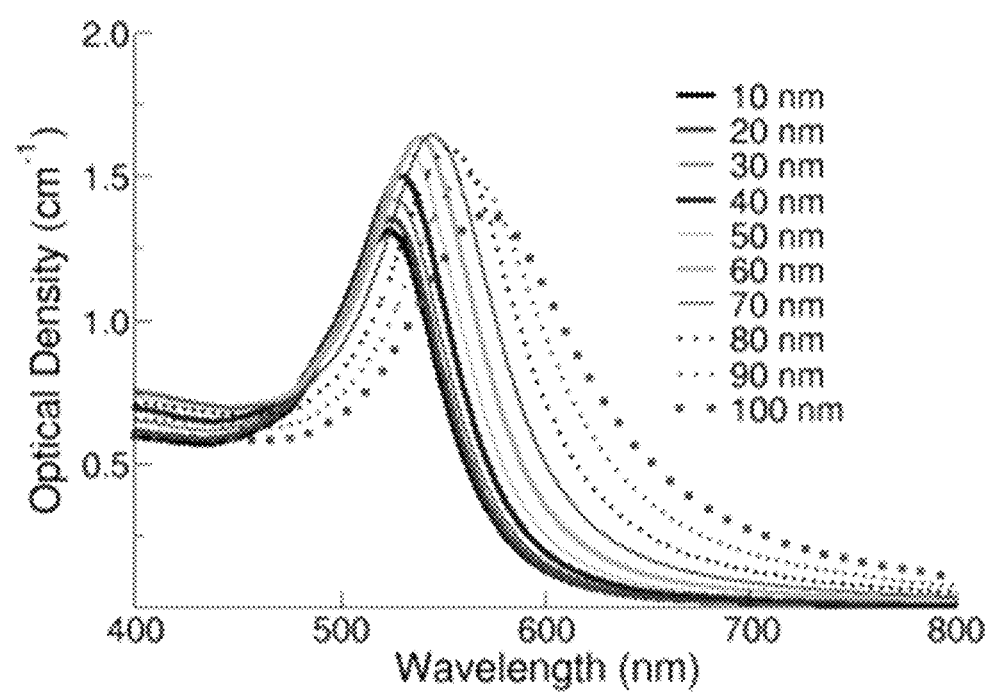
FIG. 1 is a graph of the absorbance wavelength of gold nanoparticles ranging in size from 10 nm to 100 nm.

The disclosure includes the use of polymer adhesives containing microparticles that create heat upon exposure of electromagnetic radiation (ER). Accordingly, the disclosure is directed to a system and process for accelerating the polymerization of adhesives using nanoparticles to absorb ER (e.g., light), convert the ER to heat, and provide local heating that accelerates polymerization and reduces the polymer cure time. Any application and polymer adhesive that is reactive to heat is appropriate as long as the polymer is ER transmissible and the microparticles are capable of generating heat when exposed to ER. In one aspect, the heat generated by the microparticles can be controlled by selecting the composition and size of the microparticles, and the wavelength of ER. For instance, heat may be generated as a result of the resonance of the particle, which is a function of the size of the particle. The resonance is propagated by exposing the particles to ER at the wavelength that matches particle absorption maxima. Changes in particle size will change the resonance frequency maxima of the particles. Therefore, the wavelength of ER necessary to heat the particles mixed in a polymer adhesive resin can be adjusted to accommodate the light source that may be usable or available for any particle application for the polymer adhesive.

Numerous varieties of microparticles are available and usable in polymer adhesives. For instance, metallic nanoparticles, particularly noble metal (e.g., silver, gold, platinum and palladium) nanoparticles, interact with light and such interaction is strongly dictated by nanoparticle environment and physical dimensions. Oscillating electric fields of a light ray propagating near a nanoparticle interact with the free electrons causing a concerted oscillation of the electron charge that is in resonance with the frequency of the light. As an example, for small (~30 nm size) monodisperse gold nanoparticles a surface plasmon resonance phenomenon causes an absorption of light in the blue-green portion of the spectrum (~450 nm wavelength) while red light (~700 nm wavelength) is reflected. As particle size increases, the wavelength of surface plasmon resonance related absorption shifts to longer, redder wavelengths. As particle size continues to increase toward the bulk limit, surface plasmon resonance wavelengths move into the infrared portion of the spectrum. The nanoparticle absorption peak wavelength is a monotonically-rising function of particle size only in the sub-wavelength range. Accordingly, the surface plasmon resonance can be tuned by varying the size or shape of the nanoparticles, leading to particles with tailored optical properties for different applications for adhesives. Bulk materials do not absorb electromagnetic radiation, and they are general reflective to wavelengths longer than blue-UV, depending on the metal.

Nanoparticle optical properties also depend on the refractive index near the nanoparticle surface. As the refractive index near the nanoparticle surface increases, the nanoparticle absorbance maxima shifts to longer wavelengths (known as red-shifting). Generally, the nanoparticle absorbance peak location will shift to shorter wavelengths (blue-shift) if the particles are transferred from water to air, or shift to longer wavelengths if the particles are transferred to oil. When embedded in high index materials, the extinction cross section is substantially increased. Therefore, the polymer itself will influence the resonance spectrum of the particles and the wavelength necessary to achieve the maximum resonance and heating of the polymer.

In one aspect, the disclosure is directed to the use of a nanoparticle infused polymer such as a tissue adhesive. The application of electromagnetic radiation to the polymer at the appropriate wavelength results in particle resonance and the generation of heat within the polymer, which accelerates both cure time and set time. In an application associated with the closing of a wound, the polymer bonds to the tissue edges and holds the approximated incision closed. The nanoparticle-infused polymers address the challenge associated with the time scale required for the adhesive to achieve full mechanical properties. Nanoparticle-infused adhesives and the associated application of ER allow for faster curing times that can provide mechanical strength quickly after wound closure, allowing use of the adhesive without sutures or staples and without bond failure even when the skin is under high tension. The nanoparticle infused tissue adhesives can be used in robotic and high-speed surgery. Accelerated curing of tissue adhesives at incision and wound sites can decrease the occurrence of dehiscence, improve the range of applications of tissue adhesives in wound healing (including high tension tissue sites) and reduce suturing. Therefore, the adhesives can reduce patient care time and decrease healthcare costs.

A physical barrier created by tissue adhesives may reduce microbial access to the wound and decreases the frequency of infections. In addition, the antimicrobial characteristics of silver nanoparticles add chemotherapeutic properties to the adhesive and can further decrease or eliminate infections at a site of surgery of injury.

For use in tissue adhesives, silver nanoparticles have an optical cross-section that enables their effective absorption of radiation at a wavelength that is not readily absorbed by human tissue. Controlling the loading/concentration of nanoparticles, the power of the ER, and the pulse time can regulate the heat that is locally dissipated from the particles within the polymer. For instance, human tissue absorbs red light (approximately 630-700 nm wavelength) weakly, and thus a red light source of reasonable power level is completely harmless to human tissue. In contrast, when silver nanoparticles or other metallic nanoparticles interact with red light, a fraction of the laser energy will be absorbed by the nanoparticles depending on the exact size of the particles and the precise wavelength of the light source. This absorbed energy of the exciting light source is then transferred into heat. Thus, by admixing silver nanoparticles or other metallic nanoparticles into the tissue adhesive, the heat generated by light absorption in the nanoparticles is used to heat up the polymer and accelerate the polymerization reaction. For example, the polymer cure rate can increase approximately one to ten times for every one degree increase in temperature. In one exemplary embodiment, using a laser enables the electromagnetic radiation to be focused, pulsed, and articulated to excite the polymer applied to the wound site and to control heat dissipation.

Tissue adhesives must be essentially non-toxic to animals. Cyanoacrylates, such as 2-octyl cyanoacrylate (sold as DERMABOND® adhesive), are polymer adhesives that have been widely used in medical applications. The family of cyanoacrylates also includes methyl 2-cyanoacrylate, and ethyl-2-cyanoacrylate, which commonly sold under trade names such as SUPER® glue and KRAZY® glue, and N-butyl cyanoacrylate. Other adhesives that are reactive to heat include but are not limited to, for example, epoxies, silicones, urethanes, methacrylates, and polysulfides. These adhesives are widely available and used in numerous industrial, commercial and recreational activities. Each of these adhesives and applications could benefit from the inclusion of nanoparticles and application of electromagnetic radiation to decrease cure times. For the purposes of clarity, as used herein "adhesive" includes the polymer precursor or resin, which are usually in liquid form at room temperature. When cured, the precursors for the mature polymer with maximal mechanical strength.

Figure 2:
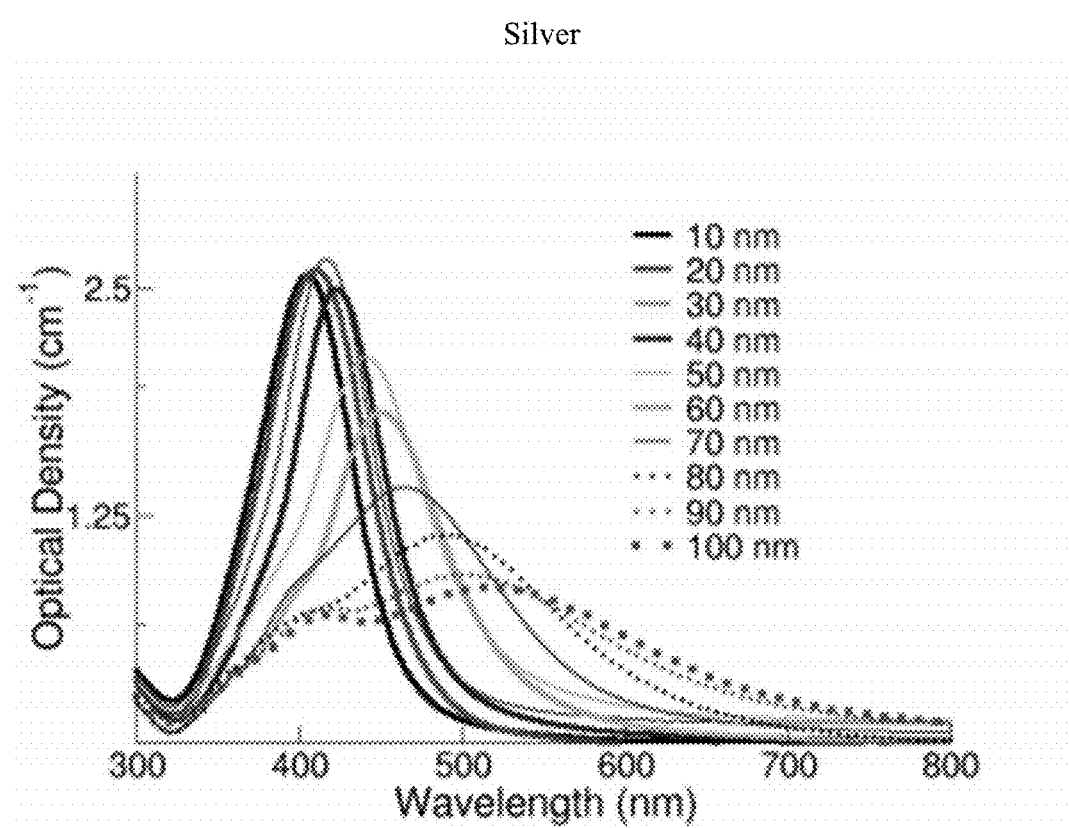
FIG. 2 is a graph of the absorbance wavelength of silver nanoparticles ranging in size from 10 nm to 100 nm.

Nanoparticles, particularly metallic nanoparticles that resonate and generate heat are widely available from a number of sources. FIGS. 1 and 2 are graphs showing, respectively, the absorption frequency of commercially available gold and silver nanoparticles that vary in size from 10 to 100 nm and having an identical mass concentration (0.02 mg/mL) (Nanocomposix, Inc., San Diego, Calif.). As particle size increases, the frequency shifts from a wavelength of about 520 nm to about 580 for gold, and from about 400 nm to about 515 nm for silver.

In addition to metal particles, other particles that may be useful include particles whose electron density can couple with electromagnetic radiation. Many fabrication processes exist for fabricating such nanoparticles, depending on the desired size and geometry. In some cases, metal coated silica or polymer-based particles have the ability to resonate and generate heat. Each of these particles can be used in polymer adhesives for a variety of applications that would benefit from faster cure times.

Electromagnetic radiation can be applied by a wide variety of sources. For example, EM sources include, but are not limited to lasers of the argon, krypton, helium-neon, helium-cadmium types, as well as tunable diode lasers. Light-emitting diodes (LEDs) are another low-cost, highly reliable illumination source. Advances in ultra-bright LEDs, mercury arc lamps, elemental arc lamps, halogen lamps, arc discharges, plasma discharges, and any combination of these provide other options for ER sources. In one embodiment, the ER source is a broad spectrum light source that includes a wavelength that matches the peak absorption wavelength of the nanoparticle.

The intensity of the light source can vary by application. For example, the total energy emitted by the source can range from about 1 mW to about 1000 mW depending on the application and the temperature tolerance of the materials that are bonded with the polymer adhesive.

In one embodiment, silver nanoparticles are admixed into cyanoacrylates polymer precursors that are liquid at room temperature. Particle loading will affect that heat dissipated by the polymer. In various embodiments of a tissue adhesive, metallic particles can be loaded into the polymer precursors at about 0.01 mg/mL to about 50 mg/mL, for example about 0.1 mg/mL to about 50 mg/mL, about 1 mg/mL to about 25 mg/mL, about 5 mg/mL to about 25 mL, and 10 mg/mL to about 20 mg/mL.

Accordingly, in one aspect, the disclosure is directed to a system that includes the polymer resin comprising a nanoparticle that has an electromagnetic radiation absorbance maximum and an electromagnetic radiation source that emits light that includes a wavelength that matches the absorbance maximum of the polymer. The system can be used in a method for at least partially curing a heat-curable polymer adhesive containing metallic nanoparticles. Complete curing of the adhesive may not be necessary for every application. Partially curing the adhesive, wherein at least 10%, 20%, 30%, 40%, 50%, 60%, 70%, 80% or 90% of the polymers are crosslinked as result of the heat generated by the nanoparticles, may be sufficient. Complete curing may then occur in the absence of the ER source and accompanying heat generation. Electromagnetic radiation may be applied to the polymer precursor, the resin, or a set or a partially cured polymer including the nanoparticles at a wavelength or range of wavelengths that include an absorption wavelength of the particle to decrease the cure time. Narrow band sources may be used as long they include the absorption wavelength of the particles.

In another aspect, the disclosure includes a method for closing a surgical incision or a wound. As part of the method, a physician or other health care practitioner approximates the wound edges and applies the nanoparticle containing pre-polymer to the tissue. With or without the use of staples or sutures, the practitioner then applies a light source having an emission spectra that includes the absorption wavelength of the particles. The light source may be applied until the polymer adhesive is partially or completely cured, thereby closing the surgical incision. In addition to intentional wounds created during surgical procedures, the tissue adhesive may be used for repairing wounds occurring from any situation. Because tissue absorbs light in the range of about 630 nm to about 700 nm in wavelength, particles that absorb light within that range can be used with reasonable light intensity levels. Accordingly, for example, gold or silver nanoparticles having diameters less than about 100 nm allow for the use of an appropriate wavelength (for example, nanoparticles with diameters less than about 90 nm, 80 nm, 70 nm, 60 nm, 50 nm, 40 nm, 30 nm, 20 nm and 10 nm).

Application of the light source should be for a duration sufficient to cure the adhesive to the desired completion. Complete curing is desirable, but depending on the time available to practitioner and patient, complete curing may be not be feasible. Sufficient bond strength may be achieve by less than complete curing in the presence of the light source, and complete curing may result after partial curing with the light source.

The necessary duration of the application of light source may be varied by the intensity of the source and the particle loading in the adhesive. For tissue adhesives, the light source, intensity, particle loading and duration should not be such that the heat generated by the process would injure the patient. For other applications, heat generation may not be a concern, which allows for a greater heat generation and even faster cure rates. The light source may be pulsed with pulse times ranging from, for example, milliseconds to seconds, depending on the application. The use of a low initial light intensity followed by high irradiation intensity, or vice versa, can also be used.

As one example of the use of the disclosed process to close a surgical wound, using 10-100 nm diameter silver nanoparticles loaded into a 2-octyl cyanoacrylate (DERMABOND®), with a loading concentration of 5-20 mg/mL, application of a 500-700 nm wavelength light source having an intensity of about 300 mW to about 700 mW for about 15 seconds to about 60 seconds will provide sufficient heat to at least partially cure the polymer. Each of these parameters may be adjusted to tune the particle size to the wavelength, and to adjust the particle loading, light intensity and time, to provide for desired polymer curing conditions.

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A method for at least partially curing a polymer adhesive containing a polymer and a metallic nanoparticle having an absorption maximum wavelength that is less than about 580 nm and greater than 400 nm, the method comprising:
    applying electromagnetic radiation to the polymer adhesive at the absorption maximum wavelength of the metallic nanoparticle that is less than about 580 nm and greater than 400 nm;
    wherein the polymer comprises acrylate, the metallic nanoparticle is a silver or gold nanoparticle, and the concentration of the metallic nanoparticle in the polymer is about 0.01 mg/mL to about 50 mg/mL.

2. The method of claim 1, wherein the metallic nanoparticle has a diameter of about 5 to about 500 nanometers.

3. The method of claim 1, wherein the polymer comprises cyanoacrylate.

4. A method for closing a wound, comprising:
    (a) applying to the wound a polymer adhesive comprising a polymer and a metallic nanoparticle having an absorption maximum wavelength that is less than about 580 nm and greater than 400 nm, wherein the concentration of the metallic nanoparticle in the polymer is about 0.01 mg/mL to about 50 mg/mL, and wherein the metallic nanoparticle is a silver or gold nanoparticle;
    (b) at least partially curing the adhesive by directing electromagnetic radiation to the adhesive at the absorption maximum wavelength of the metallic nanoparticle that is less than about 580 nm and greater than 400 nm.

5. The method of claim 4, wherein the polymer comprises cyanoacrylate.

6. The method of claim 4, wherein the metallic nanoparticle has a diameter of about 5 to about 500 nanometers.

7. The method of claim 4, wherein the wound is a surgical incision.

8. The method of claim 1, wherein the metallic nanoparticle is a silver nanoparticle with a diameter of about 5 to about 500 nanometers, and the polymer comprises cyanoacrylate.

9. The method of claim 1, wherein the concentration of the metallic nanoparticle in the polymer is about 0.1 mg/mL to about 50 mg/mL.

10. The method of claim 8, wherein the concentration of the metallic nanoparticle in the polymer is about 0.1 mg/mL to about 50 mg/mL.

11. The method of claim 4, wherein the metallic nanoparticle is a silver nanoparticle with a diameter of about 5 to about 500 nanometers, and the polymer comprises cyanoacrylate.

12. The method of claim 4, wherein the concentration of the metallic nanoparticle in the polymer is about 0.1 mg/mL to about 50 mg/mL.

13. The method of claim 4, wherein the concentration of the metallic nanoparticle in the polymer is about 1 mg/mL to about 25 mg/mL.

14. The method of claim 11, wherein the concentration of the metallic nanoparticle in the polymer is about 0.1 mg/mL to about 50 mg/mL.

15. The method of claim 11, wherein the concentration of the metallic nanoparticle in the polymer is about 1 mg/mL to about 25 mg/mL.

\* \* \* \* \*